US009713602B1

United States Patent
Wang et al.

(10) Patent No.: US 9,713,602 B1
(45) Date of Patent: Jul. 25, 2017

(54) METHOD FOR FACILITATING THE OXYGEN RELEASE OF HEMOGLOBIN-BASED BLOOD SUBSTITUTES

(71) Applicant: National Sun Yat-sen University, Kaohsiung (TW)

(72) Inventors: Chia-Chen Wang, Kaohsiung (TW); Wei-Ren Chen, Kaohsiung (TW)

(73) Assignee: NATIONAL SUN YAT-SEN UNIVERSITY, Kaohsiung (TW)

( * ) Notice: Subject to any disclaimer, the term of this patent is extended or adjusted under 35 U.S.C. 154(b) by 0 days.

(21) Appl. No.: 15/071,184

(22) Filed: Mar. 15, 2016

(51) Int. Cl.
*C07D 307/87* (2006.01)
*C07D 307/77* (2006.01)
*C07D 493/04* (2006.01)
*A61K 31/343* (2006.01)
*A61K 31/663* (2006.01)

(52) U.S. Cl.
CPC .......... *A61K 31/343* (2013.01); *A61K 31/663* (2013.01)

(58) Field of Classification Search
CPC ... C07D 307/77; C07D 307/87; C07D 493/04
See application file for complete search history.

(56) References Cited

U.S. PATENT DOCUMENTS

| 5,569,675 A * | 10/1996 | Rephaeli ............... A61K 31/22 514/512 |
| 2002/0151468 A1* | 10/2002 | Ho ...................... C07K 14/805 514/13.4 |

\* cited by examiner

*Primary Examiner* — Savitha Rao
(74) *Attorney, Agent, or Firm* — Hannah M. Tien

(57) ABSTRACT

The present invention relates to a method for increasing the oxygen release efficiency of a hemoglobin-based blood substitute by using a phthalide compound, comprising the steps of: administering to a subject in need thereof the phthalide compound or co-administering to the subject in need thereof the phthalide compound along with the hemoglobin-based blood substitute, wherein the phthalide compound has an effect of increasing the oxygen release efficiency of the hemoglobin-based blood substitute, wherein the hemoglobin-based blood substitute can be fetal hemoglobin (HbF) or other Hb variants retaining two native α subunits. The phthalide compound is used to substitute for or cooperate with 2,3-BPG, to play a role of a 2,3-BPG substitute, to act on the hemoglobin-based blood substitute to effectively substitute the function of normal hemoglobin in releasing oxygen to tissue cells, in order to maintain the cellular oxygenation level within a normal range.

8 Claims, 13 Drawing Sheets

A

B

A

B

Z-butylidenephthalide            FIG. 11A

Z-ligustilide                    FIG. 11B senkyunolide A                   FIG. 11C senkyunolide H                   FIG. 11D senkyunolide I                   FIG. 11E senkyunolide F                   FIG. 11F E-butylidenephthalide            FIG. 11G

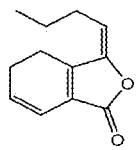 E-ligustilide     FIG. 11H
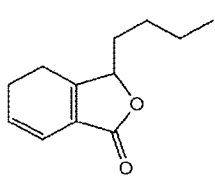 3-butylphthalide     FIG. 11I
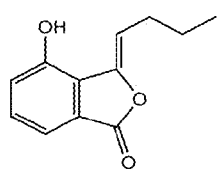 3-butylidene-4-hydrophthalide     FIG. 11J
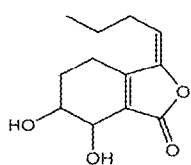 6,7-dihydroxyligustilide     FIG. 11K
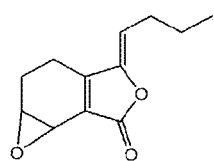 6,7-epoxyligustilide     FIG. 11L

METHOD FOR FACILITATING THE OXYGEN RELEASE OF HEMOGLOBIN-BASED BLOOD SUBSTITUTES

FIELD OF THE INVENTION

The present invention is in the medical field, relating to a method for facilitating the oxygen transport function of a hemoglobin-based blood substitute by using a drug prepared by a phthalide compound.

BACKGROUND OF THE INVENTION

Hemoglobin (Hb), the oxygen-carrying protein in erythrocytes transports oxygen from respiratory organs such as respiratory tracts and lungs and releases oxygen to organs and peripheral tissues of a human body such that the organs and the peripheral tissues can be supplied with sufficient oxygen in order to maintain normal physiological functions.

Hemoglobin of human adults is a tetramer $\alpha_2\beta_2$ consisting of four subunits, $\alpha_1$, $\alpha_2$, $\beta_1$ and $\beta_2$, wherein each subunit relies on intermolecular interactions such as intra-subunit hydrogen bonds to sustain its secondary and tertiary structures. Additionally, the inter-subunit hydrogen bonds formed among the aforementioned four subunits allow the quaternary structure of hemoglobin to be formed.

Hemoglobin can reside in two different quaternary configurations, including the relaxed form (R form) having high oxygen affinity and the tense form (T form) having low oxygen affinity. When hemoglobin is travelled to lungs through the blood circulation, hemoglobin becomes bound with oxygen and resides in the R quaternary configuration of high oxygen affinity. The oxygenated hemoglobin is then transported to organs and peripheral tissues through blood circulation and releases oxygen to organs and peripheral tissues and transforms into the T quaternary configuration of low oxygen affinity. The allostery of hemoglobin is also influenced by several allosteric factors, such as the pH value, the carbon dioxide concentration and the 2,3-BPG concentration in erythrocytes. Only when the ratio and spatial arrangement of each subunit of the hemoglobin are correct can the hemoglobin perform its normal biological function of transporting oxygen accurately in the body. Once the subunit ratio of hemoglobin is changed, or the tertiary/quaternary structures are altered, causing defect oxygen transport of hemoglobin and related hemoglobinopathies and blood diseases.

2,3-bisphosphorglycerate (2,3-BPG, or 2,3-diphosphoglycerate, 2,3-DPG; hereinafter "2,3-BPG") is the endogenous allosteric effector of hemoglobin and the most important chemical species in an erythrocyte of a human body besides the oxygen-carrying entity, hemoglobin. 2,3-BPG delicately regulates the configuration of hemoglobin by interacting with the $\beta_1$ and $\beta_2$ subunits of hemoglobin to stabilize hemoglobin in the low oxygen affinity T form to reduce the oxygen affinity of hemoglobin, thereby facilitating hemoglobin to effectively release oxygen to body organs and tissue cells.

Thalassemia is a series of recessive genetic blood disorders and a congenital disease caused by defects in globin chains, and such patients have lower contents and dysfunctional hemoglobin in the body. Thalassemia is also known as Mediterranean anemia. Although there are various types of thalassemia, the most important two types are α-thalassemia and β-thalassemia.

"β-thalassemia" is caused by insufficient synthesis of β-globin chains. Patients suffering from this type of blood disease do not develop significant symptoms during the embryonic development and newborn stages because hemoglobin in embryos or newborn babies is primarily "fetal hemoglobin (HbF)." When the newborns are grown to three to six months old, fetal hemoglobin (HbF) is gradually replaced by adult hemoglobin (HbA), and insufficient production of β-globin chains leads to insufficient production of normal hemoglobin HbA and the patients begin to develop symptoms of anemia such as pale, loss of appetite and loss of vitality. Because children suffering from this type of β-thalassemia cannot produce sufficient β-globin chains in their bodies, those who develop severe symptoms either die early or require bone marrow transplants to sustain their lives, and those who develop mild or moderate symptoms require lifelong periodical blood transfusions and long-term drug therapies to maintain their normal lives.

Sickle cell disease (SCD) is a general term for a group of genetic diseases caused by sickle hemoglobin (Hb S). In many forms of the disease, the shape of red blood cells changes because of the polymerization of abnormal sickle hemoglobin, impairing their ability to carry oxygen. This polymerization process of Hb S causes damages to the cell membrane of erythrocytes, blocks blood vessels, deprives downstream tissues of oxygen and leads to ischemia and infarction. Sickle cell disease is a chronic disease. While patients of Sickle cell disease can generally lead a normal life, they may from time to time suffer from periodical pain. The average life expectancy of these patients is shortened to about forty years. The Sickle cell disease is common in areas where malaria was once epidemic or is still epidemic. It is particularly popular in the population of sub-Saharan Africa, Caribbean, India, the Middle East and Mediterranean, especially Greece and Italy. Nevertheless, the Sickle cell disease may occur on anyone in the world, regardless of races.

Although β-thalassemia and sickle-cell anemia are common blood diseases, there remains no effective treatments up to date. Patients suffering from these blood diseases often rely on blood transfusions, and then take iron chelators to reduce the side effects caused by excessive blood transfusions, such as iron poisoning. On the other hand, the long-term blood transfusion has its drawbacks, including possible shortage of blood sources, limited shelf life of donated blood and even fatal infectious diseases caused by occasional careless blood transfusions.

Therefore, blood substitutes, which can substitute the biological function of normal hemoglobin in transporting and releasing oxygen, have been considered as a new and emerging treatment strategy for above-mentioned blood diseases in recent years. For example, it has been suggested that β-thalassemia and sickle cell anemia can be treated by reactivating or increasing the amount of fetal hemoglobin (HbF) in the body (Blood, 111, 421-429 (2008), Blood, 118, 19-27 (2011)).

At present, there exists three types of blood substitutes: perfluorocarbons (PFCs) cross-linked blood substitutes, hemoglobin-based blood substitutes and recombinant stem cell blood substitutes. Because the structures of the hemoglobin-based blood substitutes are more similar to the structure of the normal hemoglobin than the other two types, the hemoglobin-based blood substitutes are currently the most widely discussed type of blood substitutes.

In the categoty of the hemoglobin-based blood substitutes, hemoglobin variants (Hb variants) and recombinant hemoglobin (recombinant Hb, rHb) are usually suggested to be used as the blood substitutes to replace the function of normal hemoglobin in transporting and releasing oxygen, wherein the fetal hemoglobin (HbF) is the most widely discussed type of hemoglobin-based blood substitute. Just like a normal oxygen delivery system which includes the normal hemoglobin and the allosteric modulators such as 2,3-BPG to aid hemoglobin to properly release oxygen, a sound biomimetic oxygen delivery system must have a main oxygen carrying entity and an effective allosteric modulator which supports and modulates the oxygen carrying entity to release oxygen.

Although the structures of the Hb variants or the recombinant Hb to be used as the blood substitutes are similar to the structure of the normal adult hemoglobin, subtle but crucial difference exists, making them unable to entirely substitute the oxygen carrying and releasing functions of the normal adult hemoglobin. For example, the structure of fetal hemoglobin (HbF) is α2γ2. Though βHis143 is an important active site on the β subunits of normal hemoglobin (HbA) to interact with 2,3-BPG, however, βHis143 is substituted by γSer143 on γ subunits of fetal hemoglobin (HbF), resulting into reduced strength of 2,3-BPG to interact with the fetal hemoglobin (HbF) thus cannot interact with 2,3-BPG normally. Consequently, 2,3-BPG cannot serve satisfactorily as the allosteric modulator for fetal hemoglobin (HbF). This is so, because the oxygen affinity of the fetal hemoglobin (HbF) is too high, which in turn reduces the oxygen release efficiency as compared to that of adult hemoglobin (as shown in FIG. 1). Because the structural modifications for hemoglobin variants and recombinant Hb usually occur at β (non-α) subunits of Hb, 2,3-BPG, which functions by interacting with the two β subunits of hemoglobin thereby cannot modulate the oxygen affinity of these blood substitutes as effectively as that on the normal hemoglobin. Consequently, these Hb-based blood substitutes cannot fully replace the function of normal hemoglobin.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

SUMMARY OF THE INVENTION

The present invention relates to a method for preparing a composition by using a phthalide compound to facilitate a hemoglobin-based blood substitute to release oxygen, comprising the steps of: administering to a subject in need thereof the composition prepared by the phthalide compound, wherein the phthalide compound has an effect on the hemoglobin-based blood substitute to facilitate the release of oxygen, wherein the hemoglobin-based blood substitute is fetal hemoglobin (HbF) or other hemoglobin variants (Hb variants) having two α-subunits. The phthalide compound is used to substitute for and/or act with 2,3-BPG, to play a role of a 2,3-BPG substitute, to act with the hemoglobin-based blood substitute to effectively replace the biological function of normal hemoglobin in transporting and releasing oxygen to tissue cells in order to maintain the cellular oxygenation level within a normal range.

DETAILED DESCRIPTION OF THE INVENTION

Figure 12:
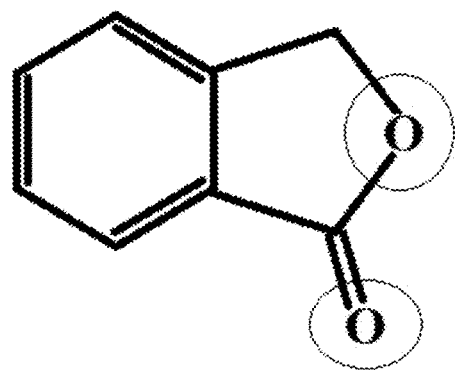
FIG. 12 is a diagram, showing the molecular structure of the functional groups of the phthalide compound.

The present invention relates to a method for using a composition prepared by a phthalide compound to facilitate a hemoglobin-based blood substitute to better release oxygen, comprising the steps of: administering to a subject in need thereof the drug prepared by a phthalide compound, wherein the phthalide compound has an effect on assisting the hemoglobin-based blood substitute to release oxygen, wherein the hemoglobin-based blood substitute is fetal hemoglobin (HbF). The phthalide compound is used to substitute for or cooperate with 2,3-BPG, to play a role of a 2,3-BPG substitute, to act with the hemoglobin-based blood substitute to effectively facilitate the release of oxygen from the hemoglobin-based blood substitute to tissue cells in order to maintain the cellular oxygenation level within a normal range. The subject is a subject in need of using the blood substitute. The phthalide compound is any compound which has the structural characteristics of the functional groups of phthalide compounds as shown in FIG. 12, wherein the circled areas are the molecular structure of the functional groups of the phthalide compounds characterized by an endocyclic oxygen and an adjacent ketone.

Figure 1:
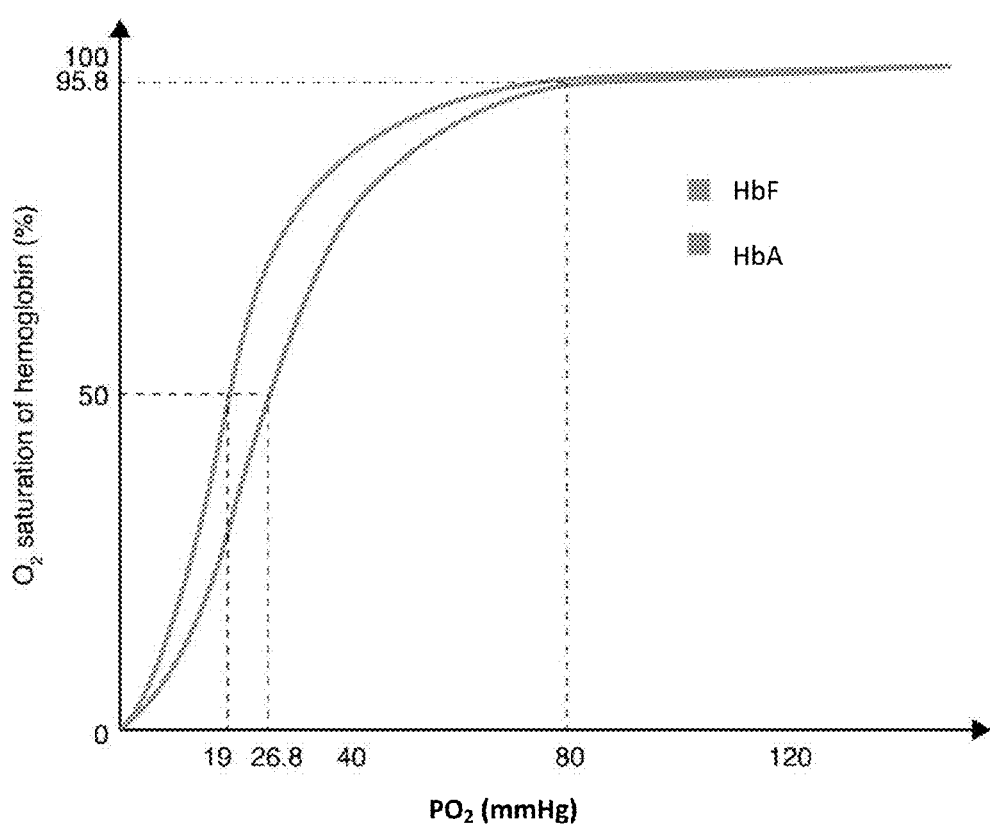
FIG. 1 shows the oxygen equilibrium curve for fetal hemoglobin (HbF) (blue curve) and adult hemoglobin (orange curve) and the corresponding $P_{50}$ values. The curves from the left to the right represent the fetal hemoglobin (HbF) and the adult hemoglobin (HbA), respectively.
Figure 2:
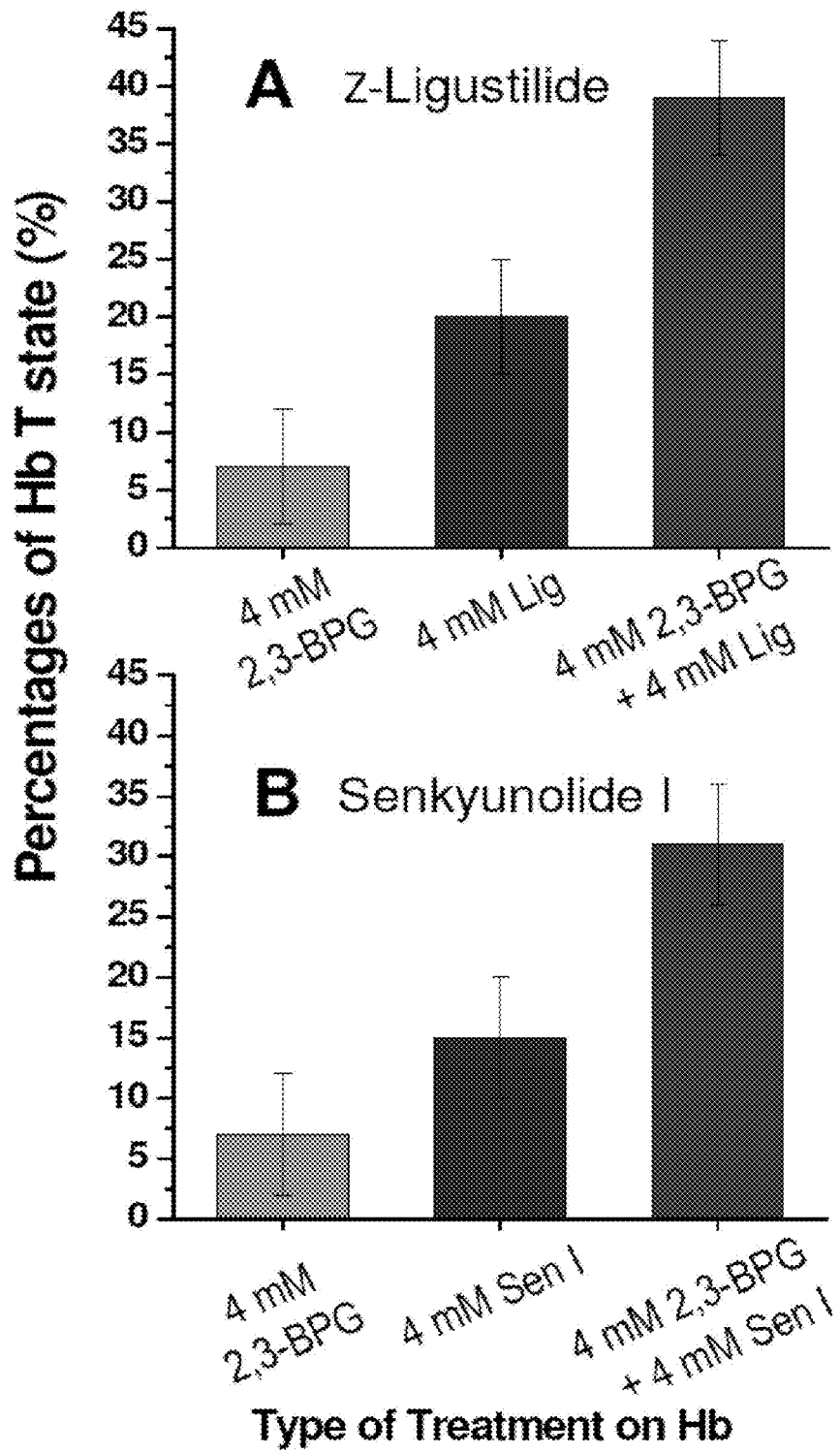
FIG. 2 shows the synergistic effect of phthalide compounds and 2,3-BPG in modulating hemoglobin allostery; A: Z-ligustilide; B: senkyunolide I.

In one preferred embodiment, the phthalide compound is able to inhibit the transformation of oxygen-carrying hemoglobin into a relaxed form, thereby stabilizing the oxygen-bound hemoglobin in a tense form of low oxygen affinity and thus aid hemoglobin to release oxygen more readily (as shown in FIG. 2).

The phthalide compound of the present invention not only substitutes for 2,3-BPG to more effectively modulate the structure and oxygen affinity of the hemoglobin-based blood substitute, but also acts together with 2,3-BPG to provide a synergistic effect on the hemoglobin-based blood substitute (as shown in FIG. 2).

In one preferred embodiment, the phthalide compound in combination with a fetal hemoglobin-based blood substitute are used as a biomimetic oxygen delivery system to be co-administered to a subject for treating blood diseases, wherein the fetal hemoglobin-based blood substitute replaces normal hemoglobin as the main oxygen-carrying entity, and the phthalide compound substitutes for or complements 2,3-BPG as the effective allosteric modulator to facilitate the oxygen transport function of the fetal hemoglobin (HbF) (making the fetal hemoglobin a more satisfactory blood substitute).

Figure 3:
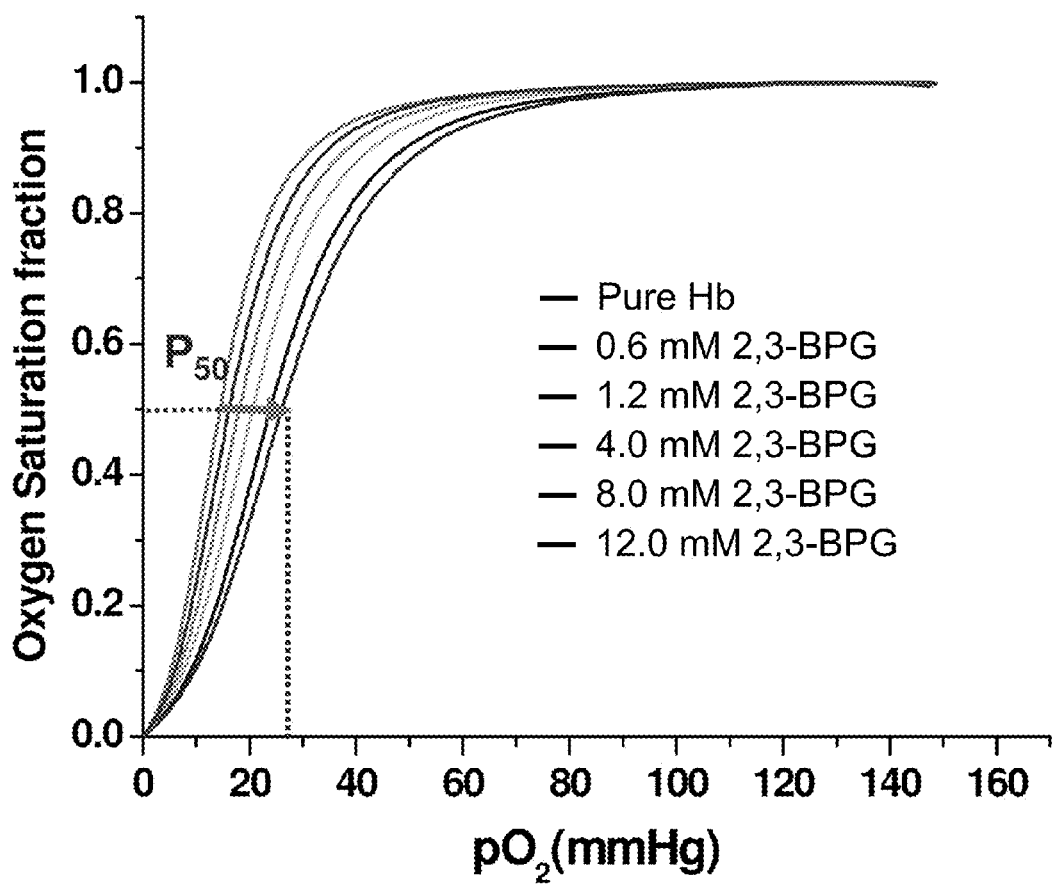
FIG. 3 shows the oxygen equilibrium curves for hemoglobin under varying concentrations of 2,3-BPG (0.2-12 mM). The curves from the left to the right represent: pure hemoglobin (Pure Hb) as the control group, 0.6 mM 2,3-BPG, 1.2 mM 2,3-BPG, 4.0 mM 2,3-BPG, 8.0 mM 2,3-BPG and 12.0 mM 2, 3-BPG, respectively.
Figure 3:
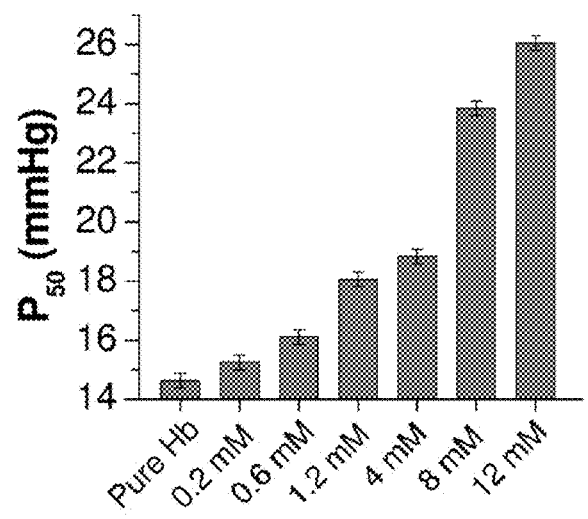
Figure 4:
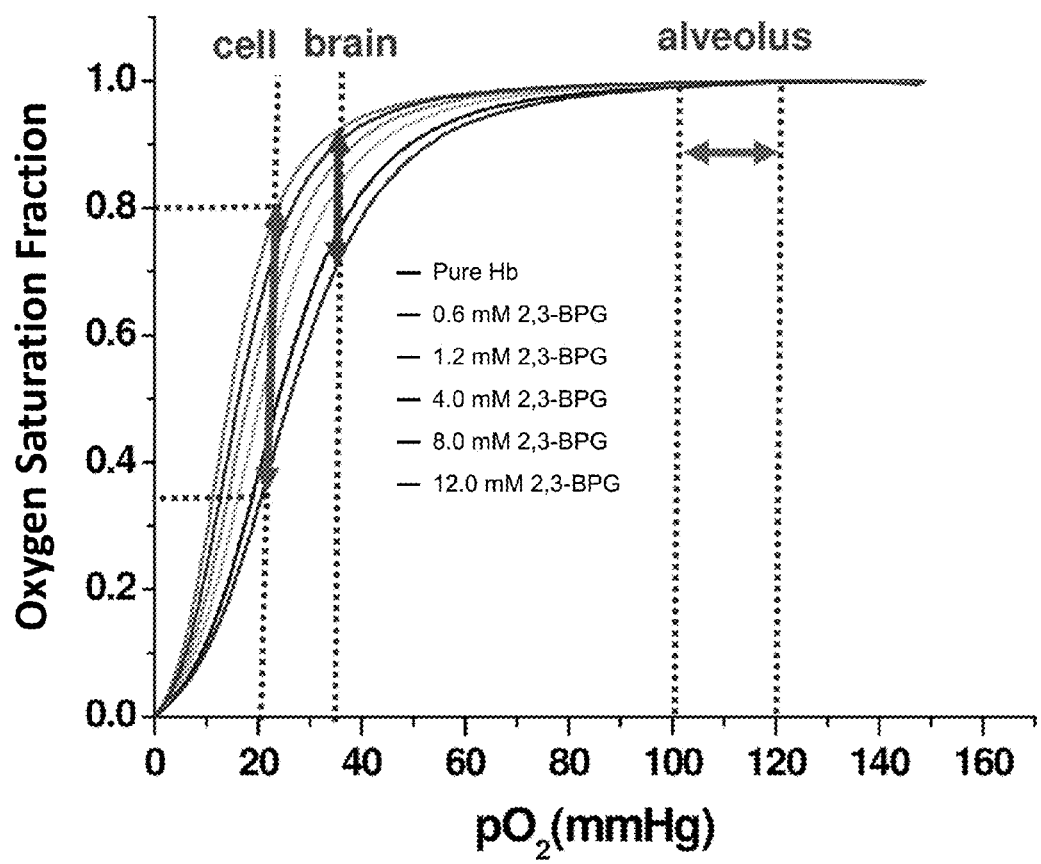
FIG. 4 shows the oxygen equilibrium curves for normal hemoglobin treated with various 2,3-BPG concentrations to illustrate that when the normal hemoglobin is modulated by 2,3-BPG how the oxygen saturation fraction is changed at various physiological oxygen partial pressures corresponding to human brain tissues, normal tissues and alveoli. The curves from the left to the right represent: pure hemoglobin (Pure Hb) as the control group, 0.6 mM 2,3-BPG, 1.2 mM 2,3-BPG, 4.0 mM 2,3-BPG, 8.0 mM 2,3-BPG and 12.0 mM 2, 3-BPG, respectively.

The oxygen affinity of hemoglobin (Hb) is commonly characterized by $P_{50}$ value. The $P_{50}$ value is the required oxygen partial pressure to achieve 50% oxygen saturation. The $P_{50}$ value of a normal adult is approximately 3.59 kPa (27 mmHg). An increased blood $PCO_2$, a decreased pH or an increased 2,3-BPG level in erythrocytes can all decrease the oxygen affinity of hemoglobin (Hb), so that the oxygen equilibrium curve shifts to the right and the $P_{50}$ value increases (as shown in FIG. 3); contrarily, when the oxygen affinity of hemoglobin (Hb) increases, the oxygen equilibrium curve shifts to the left and the $P_{50}$ value decreases. Under the normal physiological conditions, the $PO_2$ (oxygen partial pressure) of human cells is approximately 9.9-19 mmHg (J. Cell. Mol. Med., 15, 1239-1253 (2011)). By observing from the oxygen equilibrium curves of hemoglobin the effect of varying concentrations of 2,3-BPG on the oxygen saturation fraction of hemoglobin at a fixed oxygen partial pressure (as shown in FIG. 4), the effect of 2,3-BPG on increasing the oxygen release efficiency of hemoglobin (Hb) is explicitly revealed, when 12 mM of 2,3-BPG is administrated to hemoglobin, at a fixed oxygen partial pressure of 20 mmHg, the oxygen saturation fraction of hemoglobin (Hb) decreases from 80% (where no 2,3-BPG is present in hemoglobin) to 35%, indicating that the oxygen release efficiency increases from 20% to 65%.

Figure 5:
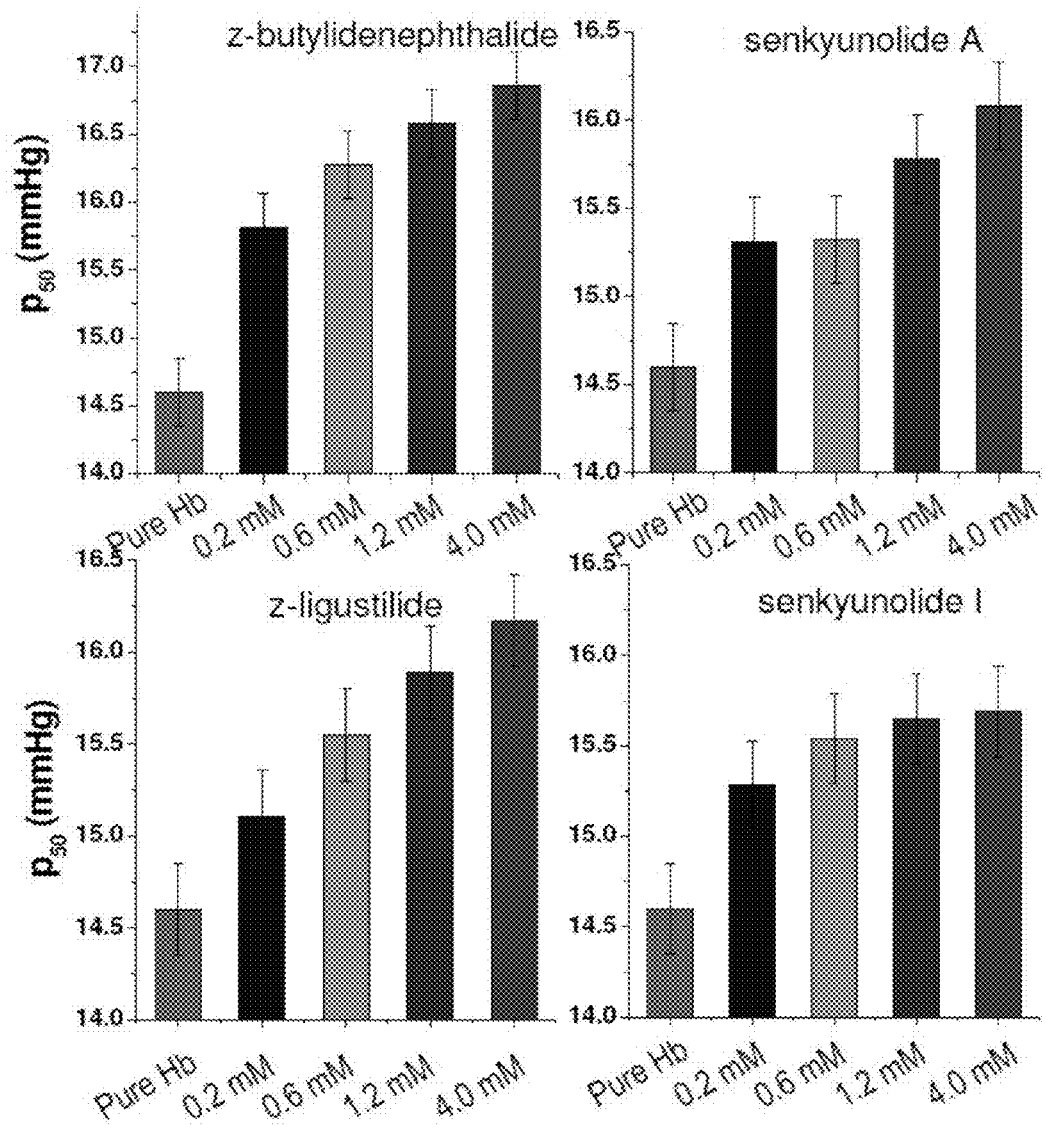
FIG. 5 shows that the $P_{50}$ value of hemoglobin increases when the concentration of phthalide compounds increases, indicating that the oxygen affinity of hemoglobin decreases and the oxygen release efficiency of hemoglobin increases with increasing concentrations of phthalide compounds.

In one preferred embodiment, the phthalide compound can effectively decrease the oxygen affinity of hemoglobin, and the higher the concentration of the phthalide compound, the higher the $P_{50}$ value and the lower the oxygen affinity are (as shown in FIG. 5).

Figure 6:
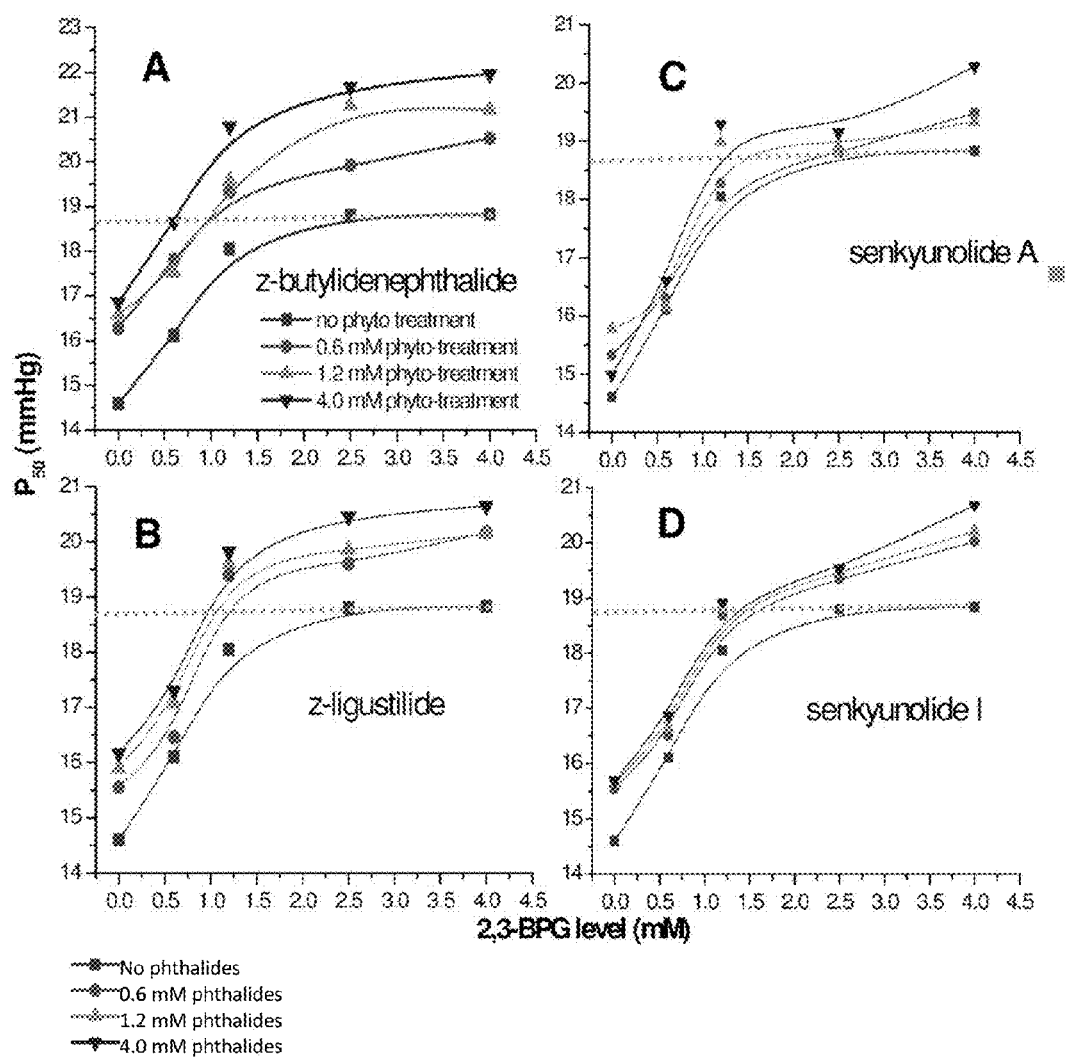
FIG. 6 shows that even at a low level of 2,3-BPG, phthalide compounds can help to modulate hemoglobin (Hb) such that Hb can reach its normal $P_{50}$ value (a comparable $P_{50}$ value under the normal level of 2,3-BPG).

In another embodiment, when no phthalide compound is treated to hemoglobin, approximately 4 mM of 2,3-BPG is required for hemoglobin to achieve a $P_{50}$ value of 18.8 mmHg; but after hemoglobin is treated with a phthalide compound, only approximately 0.6-1.2 mM of 2,3-BPG is required to achieve a similar or higher $P_{50}$ value (as shown in FIG. 6)

Figure 7:
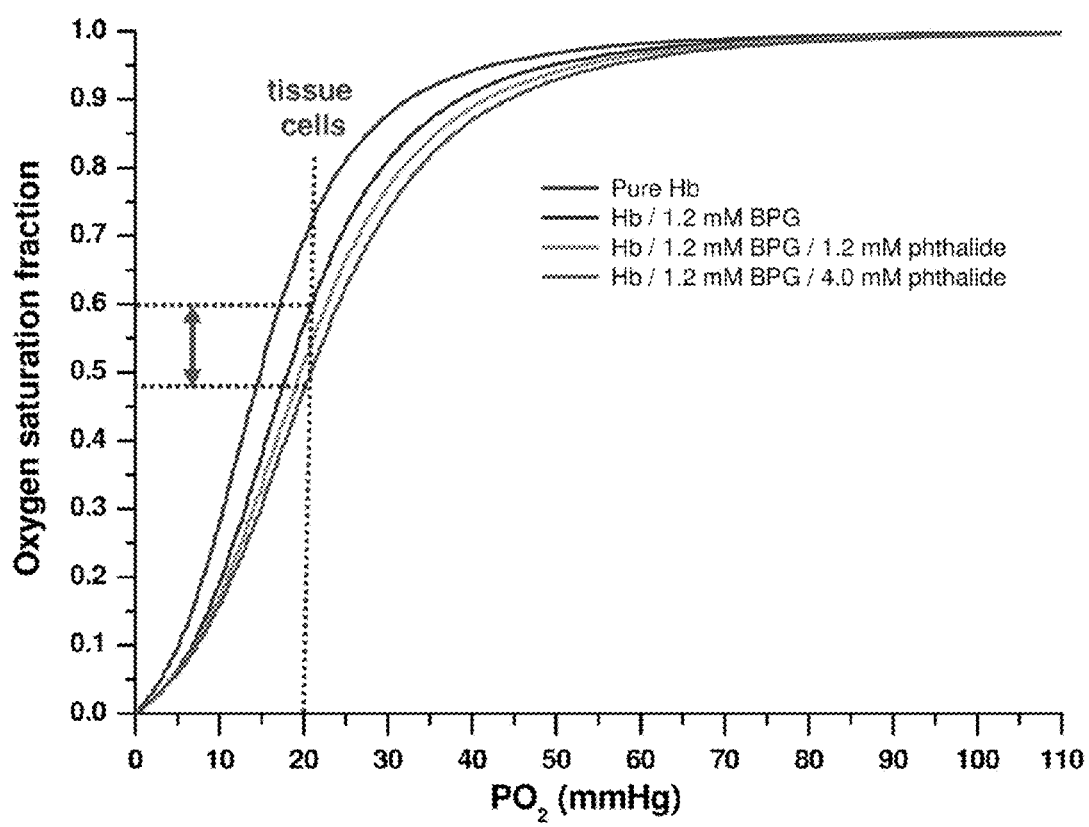
FIG. 7 shows that the oxygen equilibrium curves of normal hemoglobin can be modulated adjunctly by 2,3-BPG along with the phthalide compound, illustrating that the phthalide compound can cooperate with 2,3-BPG to decrease the blood oxygen saturation fraction and to increase the oxygen release efficiency (when the oxygen partial pressure remains unchanged). The curves from the left to the right respectively represent: pure hemoglobin (Pure Hb) as the control group, 1.2 mM 2,3-BPG, 1.2 mM 2,3-BPG and 1.2 mM phthalide compound, and 1.2 mM 2,3-BPG and 4.0 mM phthalide compound.

In another embodiment, as shown in FIG. 7, under 1.2 mM 2,3-BPG, the oxygen saturation fraction of hemoglobin at the oxygen partial pressure $PO_2$ of 20 mmHg is approximately 60/o, but after an additional phthalide compound is administered, the oxygen saturation fraction of hemoglobin decreases from 60% to approximately 47%, indicating that the oxygen release efficiency of hemoglobin increases from 40% to 53%. Therefore, it confirms that the phthalide compound is able to act together with 2,3-BPG to facilitate hemoglobin to release oxygen.

Figure 8:
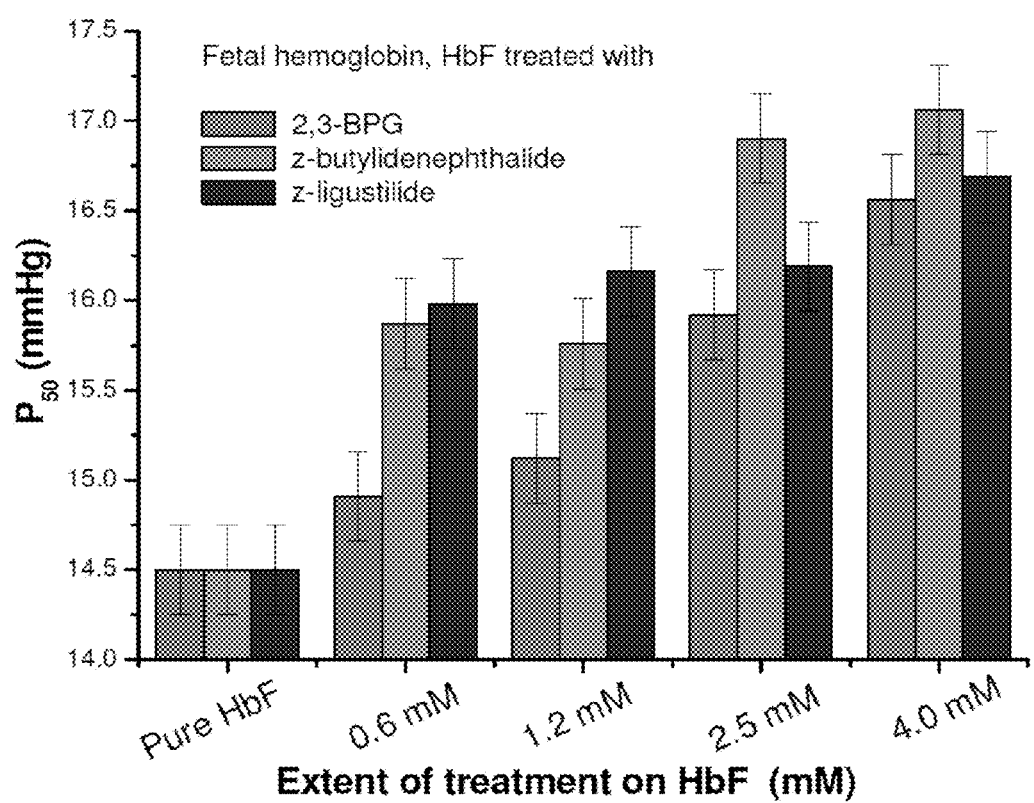
FIG. 8 shows the comparison of the effects of varying concentrations of 2,3-BPG and phthalide compounds to increase the $P_{50}$ value of fetal hemoglobin (HbF).

In another embodiment, as shown in FIG. 8, the phthalide compound not only can be used to compensate the reduced modulating effect of 2,3-BPG on the fetal hemoglobin as the blood substitute but also can provide a stronger modulating effect than 2,3-BPG on the oxygen affinity of the fetal hemoglobin (HbF). FIG. 8 compares the increased level of the $P_{50}$ value of pure fetal hemoglobin (Pure HbF) and the fetal hemoglobin (HbF) treated with either 2,3-BPG or the phthalide compound. As clearly shown in FIG. 8, Z-butylidenephthalide (orange columns) and Z-ligustilide (purple columns) have a stronger modulating effect than 2,3-BPG (gray columns) on the oxygen affinity of the fetal hemoglobin (HbF).

Figure 9:
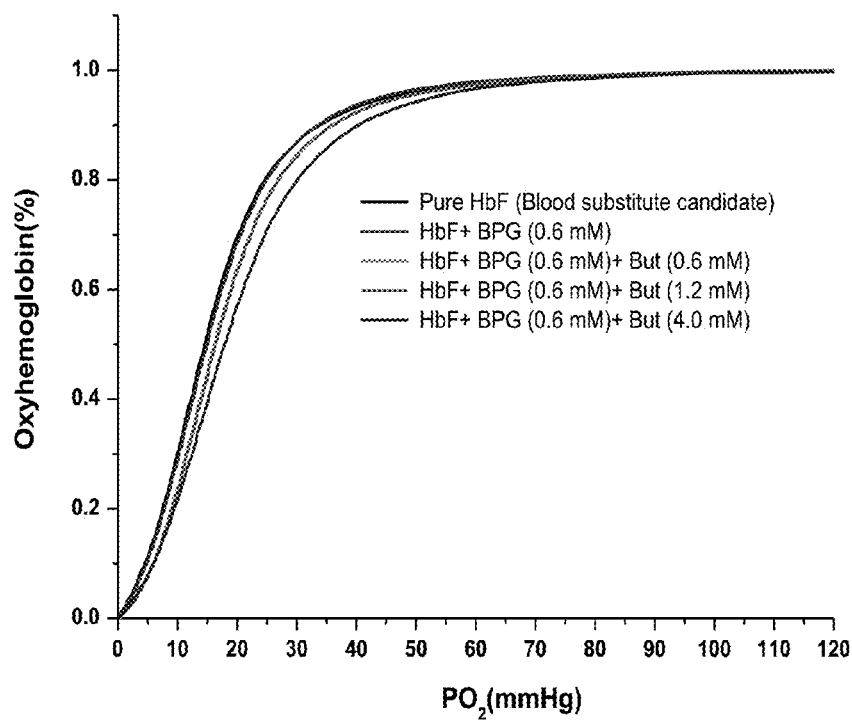
FIG. 9 shows the effect of Z-butylidenephthalide (indicated as "But" in the drawing) on shifting the oxygen equilibrium curve for fetal hemoglobin (HbF) to the right; A: the curves from the left to the right respectively represent: pure fetal hemoglobin (Pure HbF) as the control group, fetal hemoglobin (HbF) treated with 0.6 mM 2,3-BPG, fetal hemoglobin (HbF) treated with 0.6 mM 2,3-BPG and 0.6 mM of Z-butylidenephthalide, fetal hemoglobin (HbF) treated with 0.6 mM 2,3-BPG and 1.2 mM Z-butylidenephthalide, fetal hemoglobin (HbF) treated with 0.6 mM 2,3-BPG and 4.0 mM Z-butylidenephthalide; B: the curves from the left to the right respectively represent: pure fetal hemoglobin (Pure HbF) as the control group, fetal hemoglobin (HbF) treated with 2.5 mM 2,3-BPG, fetal hemoglobin (HbF) treated with 2.5 mM 2,3-BPG and 0.6 mM of Z-butylidenephthalide, fetal hemoglobin (HbF) treated with 2.5 mM 2,3-BPG and 1.2 mM of Z-butylidenephthalide, fetal hemoglobin (HbF) treated with 2.5 mM 2,3-BPG and 4.0 mM of Z-butylidenephthalide.
Figure 9:
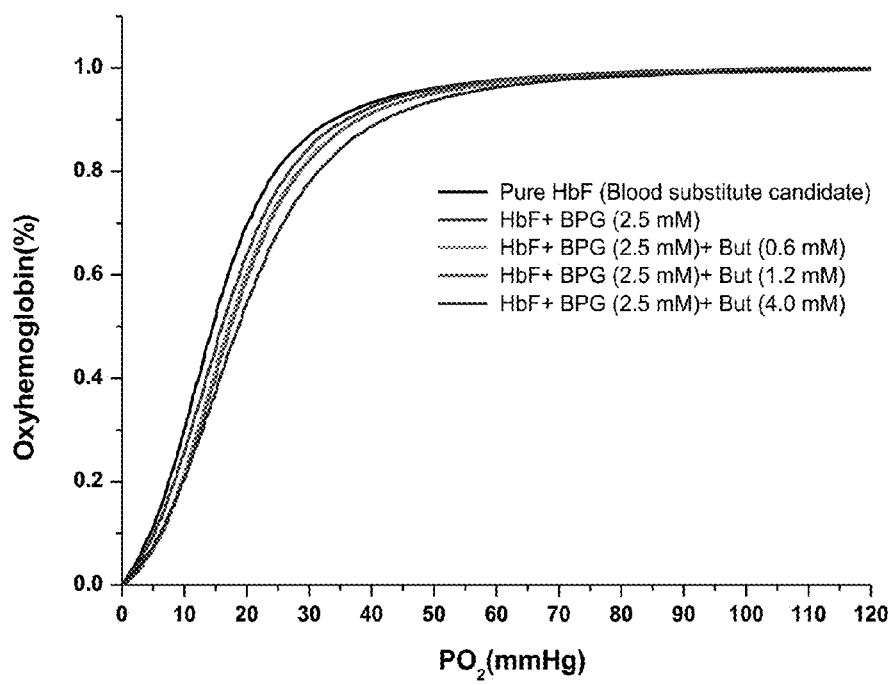

In another embodiment, as shown in FIG. 9, Z-butylidenephthalide (indicated as "But" in the drawing) can effectively shift the oxygen equilibrium curve for the fetal hemoglobin (HbF) to the right, which shows that when 2,3-BPG has a weaker modulating effect on the fetal hemoglobin (HbF), Z-butylidenephthalide can aid the fetal hemoglobin (HbF) to achieve the same oxygen release efficiency as the normal hemoglobin.

Figure 10:
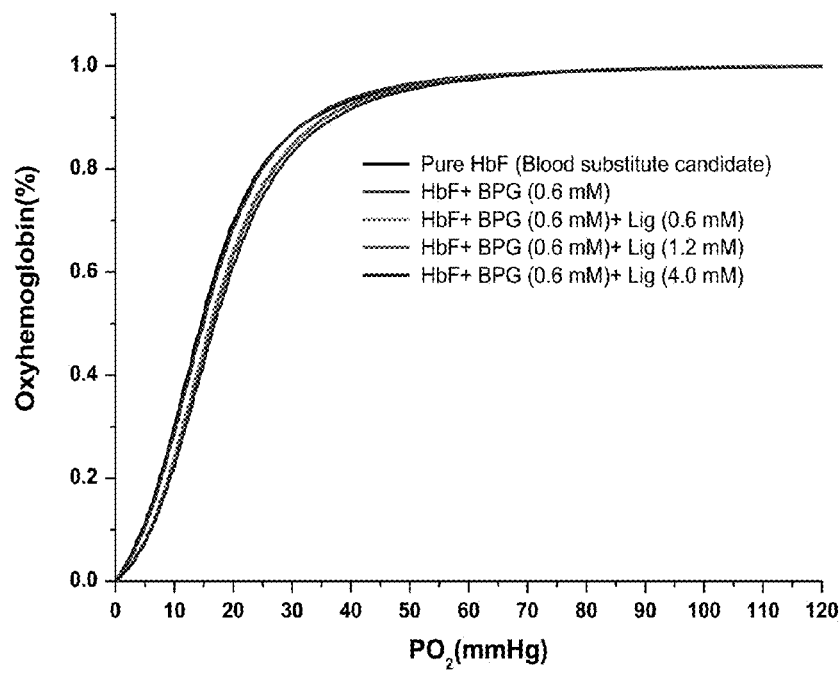
FIG. 10 shows the effect of Z-ligustilide (indicated as "Lig" in the drawing) on shifting the oxygen equilibrium curves for fetal hemoglobin (HbF) to the right; A: the curves from the left to the right respectively represent: pure fetal hemoglobin (Pure HbF) as the control group, fetal hemoglobin (HbF) treated with 0.6 mM 2,3-BPG; fetal hemoglobin (HbF) treated with 0.6 mM 2,3-BPG and 0.6 mM of Z-ligustilide; fetal hemoglobin (HbF) treated with 0.6 mM 2,3-BPG and 1.2 mM Z-ligustilide; fetal hemoglobin (HbF) treated with 0.6 mM 2,3-BPG and 4.0 mM Z-ligustilide. B: the curves from the left to the right respectively represent: pure fetal hemoglobin (Pure HbF) as the control group; fetal hemoglobin (HbF) treated with 2.5 mM 2,3-BPG, fetal hemoglobin (HbF) treated with 2.5 mM 2,3-BPG and 0.6 mM of Z-ligustilide, fetal hemoglobin (HbF) treated with 2.5 mM 2,3-BPG and 1.2 mM of Z-ligustilide, fetal hemoglobin (HbF) treated with 2.5 mM 2,3-BPG and 4.0 mM of Z-ligustilide.
Figure 10:
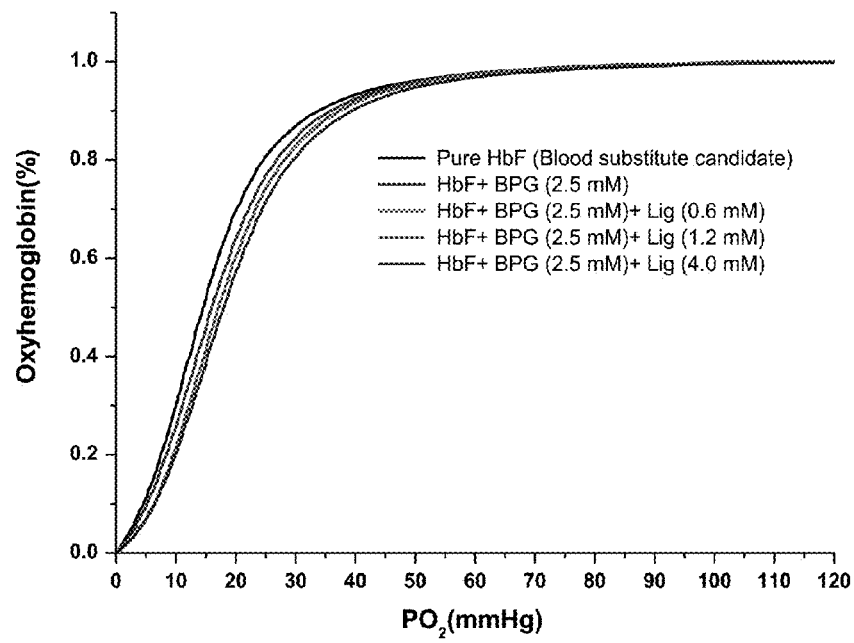

In another embodiment, as shown in FIG. 10, Z-ligustilide (indicated as "Lig" in the drawing) can effectively shift the oxygen equilibrium curve for the fetal hemoglobin (HbF) to the right, which shows that when 2,3-BPG has a weaker modulating effect on the fetal hemoglobin (HbF), Z-ligustilide can aid the fetal hemoglobin (HbF) to achieve the same oxygen release efficiency as the normal hemoglobin.

Therefore, the method of the present invention is to use a drug prepared by the phthalide compound to substitute for or act with 2,3-BPG as an allosteric modulator to improve the oxygen release efficiency of hemoglobin-based blood substitute, to increase oxygen transport efficiency, thereby facilitating the release of oxygen from the hemoglobin-based blood substitute to various organs and tissues more easily, which in turn can enhance the ability of the hemoglobin-based blood substitute for treating blood diseases such as sickle-cell anemia and thalassemia.

EXAMPLES

The examples and figures mentioned in the following text are used to illustrate the technical content, characteristics and advantages of the present invention and are not used to limit the present invention.

Figure 11:
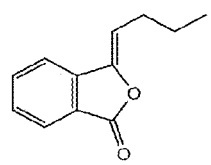
FIGS. 11A-11L show the molecular structures of twelve phthalide compounds; 11A: Z-butylidenephthalide; 11B: Z-ligustilide; 11C: senkyunolide A; 11D: senkyunolide H; 11E: senkyunolide I; 11F: senkyunolide F; 11G: E-butylidenephthalide; 11H: E-ligustilide; 11I: 3-butylphthalide; 11J: 3-butylidene-4-hydrophthalide; 11K: 6,7-dihydroxyligustilide; 11L: 6,7-epoxyligustilide.
Figure 11:
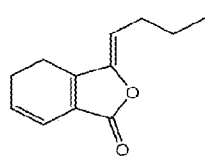
Figure 11:
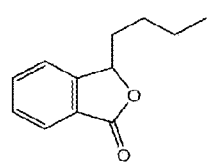
Figure 11:
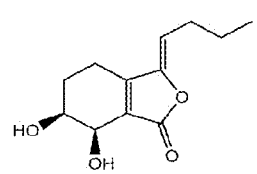
Figure 11:
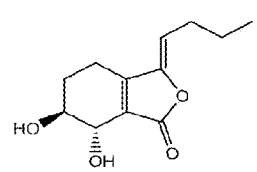
Figure 11:
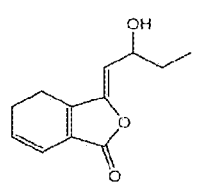
Figure 11:
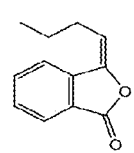

The phthalide compound provided by the present invention could be any compound having the characteristics of the molecular structure of the phthalide compound, such as Z-butylidenephthalide (as shown in FIG. 11A), Z-ligustilide (as shown in FIG. 11B), senkyunolide A (as shown in FIG. 11C), senkyunolide H (as shown in FIG. 11D), senkyunolide I (as shown in FIG. 11E), senkyunolide F (as shown in FIG. 11F), E-butylidenephthalide (as shown in FIG. 11G), E-ligustilide (as shown in FIG. 11H), 3-butylphthalide (as shown in FIG. 11I), 3-butylidene-4-hydrophthalide (as shown in FIG. 11J), 6,7-dihydroxyligustilide (as shown in FIG. 11K) and 6,7-epoxyligustilide (as shown in FIG. 11L).

The oxygen affinity of hemoglobin is commonly characterized by $P_{50}$ value. The $P_{50}$ value is the required oxygen partial pressure for hemoglobin to achieve 50% oxygen saturation. The $P_{50}$ value of a normal adult is approximately 3.59 kPa (27 mmHg). An increased blood $PCO_2$, a decreased pH or an increased concentration of 2,3-BPG in erythrocytes could all decrease the oxygen affinity of hemoglobin, as a result, the oxygen equilibrium curve shifted to the right and the $P_{50}$ value increased (as shown in FIG. 3); contrarily, when the oxygen affinity of hemoglobin increased, the oxygen equilibrium curve shifted to the left and the $P_{50}$ value decreased. In a preferred example, the phthalide compound could effectively decrease the oxygen affinity of hemoglobin, and the higher the concentration of the phthalide compound, the higher the $P_{50}$ value and the lower the oxygen affinity are (as shown in FIG. 7).

In another example, when no phthalide compound was treated to hemoglobin, approximately 4 mM of 2,3-BPG was required for hemoglobin to achieve a $P_{50}$ value of 18.8 mmHg; but after hemoglobin was treated with a phthalide compound, only approximately 0.6-1.2 mM of 2,3-BPG was required to achieve a similar or higher $P_{50}$ value (as shown in FIG. 6).

In another example, as shown in FIG. 7, under 1.2 mM 2,3-BPG, the oxygen saturation level fraction of hemoglobin at the oxygen partial pressure $PO_2$ of 20 mmHg was approximately 60%, but after an additional phthalide compound was administered, the oxygen saturation fraction of hemoglobin decreased from 60% to approximately 47%, indicating that the oxygen release efficiency of hemoglobin increased from 40% to 53%. Therefore, it confirmed that the phthalide compound was able to act together with 2,3-BPG to facilitate hemoglobin to release oxygen.

Under normal conditions, the oxygen partial pressure $PO_2$ of a human brain is approximately 33.8±2.6 mmHg (J. Cell. Mol. Med., 15, 1239-1253 (2011)), but as could be seen from the hemoglobin oxygen equilibrium curve (as shown in FIG. 4), after treating hemoglobin with varying concentrations of 2,3-BPG, the oxygen saturation fraction of hemoglobin at the oxygen partial pressure corresponding to the brain physiological $PO_2$ decreased approximately from 90% to 70%, indicating that the oxygen release efficiency increased from 10% to 30%. The oxygen release efficiency of normal cells was increased approximately from 20% to 65%.

In one example, the phthalide compound could be used adjunctly with other compounds which were capable of stabilizing the oxygen-bound hemoglobin-based blood substitute in the low oxygen affinity T form to increase the oxygen release efficiency by decreasing the oxygen affinity of the hemoglobin-based blood substitute.

By modulating the α1/α2 interface (rather than β1/β2) of fetal hemoglobin, the phthalide compound could compensate the reduced oxygen affinity modulating effect of 2,3-BPG on the fetal hemoglobin. In one preferred example, the increased level of the $P_{50}$ values of pure fetal hemoglobin (Pure HbF), fetal hemoglobin (HbF) treated with 2,3-BPG and fetal hemoglobin (HbF) treated with the phthalide compound were compared, and the results showed that the oxygen affinity modulating effects of Z-butylidenephthalide and Z-ligustilide on the fetal hemoglobin were both higher than that of 2,3-BPG on the fetal hemoglobin (as shown in FIG. 8).

In another example, Z-butylidenephthalide could effectively shift the oxygen equilibrium curve of the fetal hemoglobin (HbF) to the right, which showed that even when the modulating effect of 2,3-BPG on the fetal hemoglobin (HbF) was not as effective as that on the normal hemoglobin, Z-butylidenephthalide could effectively modulate the fetal hemoglobin (HbF) such that the fetal hemoglobin can achieve the same oxygen release efficiency as the normal hemoglobin. Also, the higher the concentration of Z-butylidenephthalide, the oxygen equilibrium curve shifted more toward the right, indicating that the oxygen release efficiency became also higher (as shown in FIG. 9).

In another example, Z-ligustilide could effectively shift the oxygen equilibrium curve for the fetal hemoglobin (HbF) to the right, which showed that even when the modulating effect of 2,3-BPG on the fetal hemoglobin (HbF) was not as effective as that on the normal hemoglobin, Z-ligustilide could effectively modulate the fetal hemoglobin (HbF) such that the fetal hemoglobin can achieve the same oxygen release efficiency as the normal hemoglobin. Also, the higher the concentration of Z-ligustilide, the oxygen equilibrium curve shifted more toward the right, indicating that the oxygen release efficiency became also higher (as shown in FIG. 10).

In another preferred example, the phthalide compound was co-administered along with a hemoglobin-based blood substitute to a subject, wherein the administration methods comprised oral administration, injection and incorporating the phthalide compounds into the blood substitute; the timing for administration of the phthalide compound to a subject could be administered before, concurrently or after the administration of the blood substitute.

In one example, the phthalide compound could be used together with other compounds which were capable of stabilizing the oxygen-bound hemoglobin-based blood substitute in the T form and decreasing the oxygen affinity of hemoglobin-based blood substitute to increase the oxygen release efficiency of hemoglobin.

In another example, 2,3-BPG and the phthalide compound were co-administered along with the hemoglobin-based blood substitute to a subject, wherein the administration method comprised oral administration, injection and incorporating 2,3-BPG and the phthalide compound into the hemoglobin-based blood substitute.

In summary, the present invention provided a method for preparing a composition by using a phthalide compound to increase the oxygen transport function of a hemoglobin-based blood substitute, wherein the phthalide compound had an effect on increasing the oxygen release efficiency of the hemoglobin-based blood substitute, wherein the hemoglobin-based blood substitute was fetal hemoglobin (HbF) or other Hb variants or recombinant Hb having two α subunits. The phthalide compound was used to substitute for or cooperate with 2,3-BPG, to play a role as a 2,3-BPG substitute, to enable the hemoglobin-based blood substitute to effectively release oxygen to organs and peripheral tissue cells, thereby maintaining the cellular oxygenation level in a normal range.

The content aforementioned is illustrated for fully realizing the present invention. However, the present invention may be implemented in many different forms and should not be construed as limited to the embodiments set forth herein; one skilled in the art may modify and vary the embodiments without departing from the spirit and scope of the present invention, therefore, the embodiments should not be construed as the limitation of the claims

What is claimed is:

1. A method for increasing oxygen transport function of a hemoglobin-based blood substitute, comprising administering a phthalide compound to a subject in need thereof, wherein the phthalide compound increases oxygen release efficiency of the hemoglobin-based blood substitute, wherein the phthalide compound is selected from the group consisting of Z-butylidenephthalide, Z-ligustilide, senkyunolide A, senkyunolide H, senkyunolide I, senkyunolide F, E-butylidenephthalide, E-ligustilide, 3-butylphthalide, 3-butylidene-4-hydrophthalide, 6,7-dihydroxligustilide and 6,7-epoxyligustilide.

2. The method of claim 1, wherein the hemoglobin is fetal hemoglobin (HbF).

3. The method of claim 2, wherein the phthalide compound provides a synergistic effect with the 2,3-bisphosphorglycerate on modulating the fetal hemoglobin (HbF).

4. A method for increasing oxygen release efficiency of a hemoglobin-based blood substitute, comprising co-administering a phthalide compound and a blood substitute to a subject in need thereof, wherein the phthalide compound has an effect of increasing the oxygen release efficiency of the hemoglobin-based blood substitute, wherein the phthalide compound is selected from the group consisting of Z-butylidenephthalide, Z-ligustilide, senkyunolide A, senkyunolide H, senkyunolide I, senkyunolide F, E-butylidenephthalide, E-ligustilide, 3-butylphthalide, 3-butylidene-4-hydrophthalide, 6,7-dihydroxyligustilide and 6,7-epoxyligustilide.

5. The method of claim 4, wherein the hemoglobin-based blood substitute is fetal hemoglobin (HbF).

6. The method of claim 4, wherein the method for administering the phthalide compound to the subject in need thereof comprises oral administration, injection and incorporation of the phthalide compound into the hemoglobin-based blood substitute.

7. The method of claim 4, which further comprises co-administering 2,3-bisphosphorglycerate and the phthalide compound along with the hemoglobin-based blood substitute to the subject in need thereof, wherein the method of administration comprises oral administration, injection and incorporation of the 2,3-BPG and the phthalide compound into the hemoglobin-based blood substitute.

8. The method of claim 4 or 6, wherein the phthalide compound provides a synergistic effect with 2,3-bisphosphorglycerate on the fetal hemoglobin (HbF).

* * * * *